United States Patent [19]

Beurrier

[11] Patent Number: 5,306,281
[45] Date of Patent: Apr. 26, 1994

[54] SUTURING CASSETTE DEVICE

[75] Inventor: Henry R. Beurrier, Far Hills, N.J.

[73] Assignee: Merrimac Industries, Inc., West Caldwall, N.J.

[21] Appl. No.: 938,916

[22] Filed: Aug. 31, 1992

[51] Int. Cl.$^5$ ............................................. A61B 17/00
[52] U.S. Cl. ................................... 606/144; 606/139; 606/223; 112/80.03; 112/116
[58] Field of Search .............. 606/139, 144, 145, 147, 606/148, 185, 187, 222-227; 112/80.03, 169

[56] References Cited

U.S. PATENT DOCUMENTS

| | | | |
|---|---|---|---|
| 4,557,265 | 12/1985 | Andersson | 606/145 |
| 4,747,358 | 5/1988 | Moll et al. | 112/177 |
| 4,899,746 | 2/1990 | Brunic | 606/144 |

FOREIGN PATENT DOCUMENTS

| | | | |
|---|---|---|---|
| 0835429 | 6/1981 | U.S.S.R. | 606/144 |
| 0018602 | of 1908 | United Kingdom | 606/139 |
| WO86/03396 | 6/1986 | World Int. Prop. O. | 606/224 |

Primary Examiner—Stephen C. Pellegrino
Assistant Examiner—Jeffrey A. Schmidt
Attorney, Agent, or Firm—Pennie & Edmonds

[57] ABSTRACT

A mechanical apparatus for suturing biological tissue including a cassette housing, a continuous loop belt mounted for circulation therein, an arcuate needle mounted within the cassette for 360° rotation having a plurality of closely spaced projecting means for engaging the continuous loop belt, and means for circulating the continuous loop belt. The cassette housing is easily attachable to and detachable from the means for circulating the continuous loop belt.

14 Claims, 6 Drawing Sheets

SUTURING CASSETTE DEVICE

TECHNICAL FIELD

The present invention generally relates to surgical instruments, and more particularly, to suturing devices.

BACKGROUND OF THE INVENTION

Various forms of suturing devices are known in the art, and those which utilize a curved needle and/or a cassette are particularly relevant to the present invention. For example, U.S. Pat. Nos. 4,027,608 and 4,235,177 to Arbuckle, 4,406,237 to Eguchi et al., 4,417,532 to Yasukata, and 4,440,171 to Nomoto et al. describe suturing devices that use a reciprocating curved needle and means for looping and/or securing a suture thread; U.S. Pat. No. 4,557,265 to Andersson, describes a suturing device and method for moving an arcuate needle in a closed path through opposite edges of a tissue incision to complete a suture; U.S. Pat. No. 4,899,746 to Brunk describes a suturing device incorporating a curved needle into a motor driven cassette; and, U.K. Patent No. 18,602 to Mitchell describes a suturing device utilizing an arcuate needle having two recesses on remote ends of the needle which are capable of being engaged by two mating tooth-like projections on the surface of a band.

There are various drawbacks, however, with the prior art. For instance, the apparatuses described in Arbuckle, Eguchi, Yasukata and Nomoto utilize a reciprocating needle. These devices, therefore, require an added mechanism for looping and/or securing the suture thread. The looping mechanism makes it impractical to change needles in these instruments quickly and efficiently during an operation because, for example, the looping mechanism would have to be repositioned to engage a different sized needle. In fact, it may not be possible to change needle sizes at all in some of these devices. Notwithstanding this problem, the instruments are also less efficient for tying a suture knot when compared to the automatic knot tying capabilities of the present invention. Moreover, these looping mechanisms unnecessarily increase the size of these suturing devices making them more difficult to operate, burdensome, and impractical for certain suturing procedures.

Instruments, such as those described in Andersson and Brunk, do not require the extra looping mechanism because they utilize a fully rotating arcuate suturing needle. Indeed, it is also possible to change needles quickly with the apparatus described in Brunk. These instruments, however, pose a potential health risk to surgery patients. These instruments utilize friction rollers to drive a curved suturing needle through biological tissue. The suturing needle, however, does not positively engage the friction rollers (and vice versa), and therefore, the needle is not prevented from slipping and embedding in a patient. This most likely occurs when the needle encounters a friction force from the tissue being sutured greater than the friction force of the rollers driving the needle. Needle slippage can be avoided by ensuring positive engagement of the needle with a needle driving mechanism similar to the apparatus described in Mitchell. However, even the Mitchell apparatus poses the same potential risk of embedding the needle in a patient where either tooth on the band fails to engage with its sole mating recess on the needle. Therefore, as evidenced by the prior art, there is a need for a suturing apparatus which overcomes these apparent problems.

SUMMARY OF THE INVENTION

In light of the aforementioned drawbacks with the prior art, it is a particular object of the present invention to prevent the suture needle from slipping. To satisfy this objective the present invention comprises a body member wherein there is a continuous loop belt, and an arcuate suturing needle, mounted for 360° rotation, having a plurality of closely spaced projecting means for positively engaging the belt. The needle advances through its suturing rotation when the drive belt passes over the needle. By presetting a suture thread about the foot area of the cassette, the present invention semi-automatically ties a suture knot thereby making obsolete the need for an additional looping mechanism.

A separate but important object of this invention is to provide a quick and efficient means for changing needle sizes. To achieve this objective the present invention provides a suturing apparatus as described above, wherein the body member comprises a cassette housing. The belt is mounted for circulation, and the needle is mounted for 360° rotation therein. The cassette housing is easily attachable to and detachable from a means for driving the continuous loop belt. It therefore provides an efficient means for changing a needle and belt, which is important for surgery requiring the use of various needle sizes during the operation.

An additional object of this invention is to prevent the spread of infection to patients and doctors alike. With the needle contained within the cassette, a user of the device is protected from the transfer of infection, such as, by sticking himself with the needle. This is especially important with the prevalence of the AIDS virus today. The cassette also provides an efficient means of disposing of a used needle and belt. For purposes of conservation it is also contemplated that the cassette can be factory rebuilt after use.

An additional object the present invention is to prevent the possibility of suturing tissue to underlying organs. To achieve this objective two pieces slideably mounted to the foot area of the cassette are capable of pinching together two sides of tissue to be sutured. This draws the tissue up and away from underlying organs. It is also contemplated that a vacuum can be incorporated into the foot area of the cassette to accomplish the same results.

DETAILED DESCRIPTION OF THE PREFERRED EMBODIMENT

Figure 1:
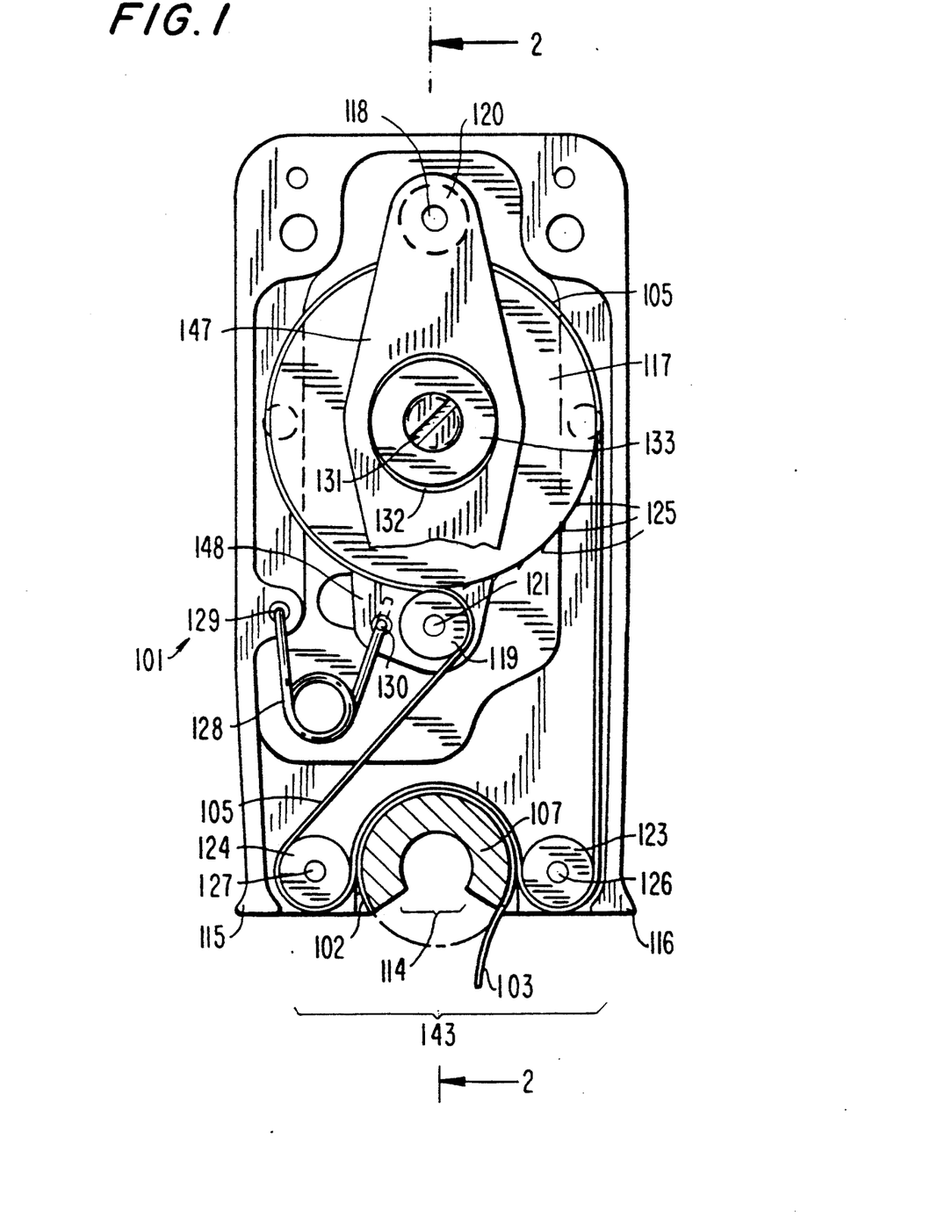
FIG. 1 is a plan view of the cassette according to the present invention.
Figure 2:
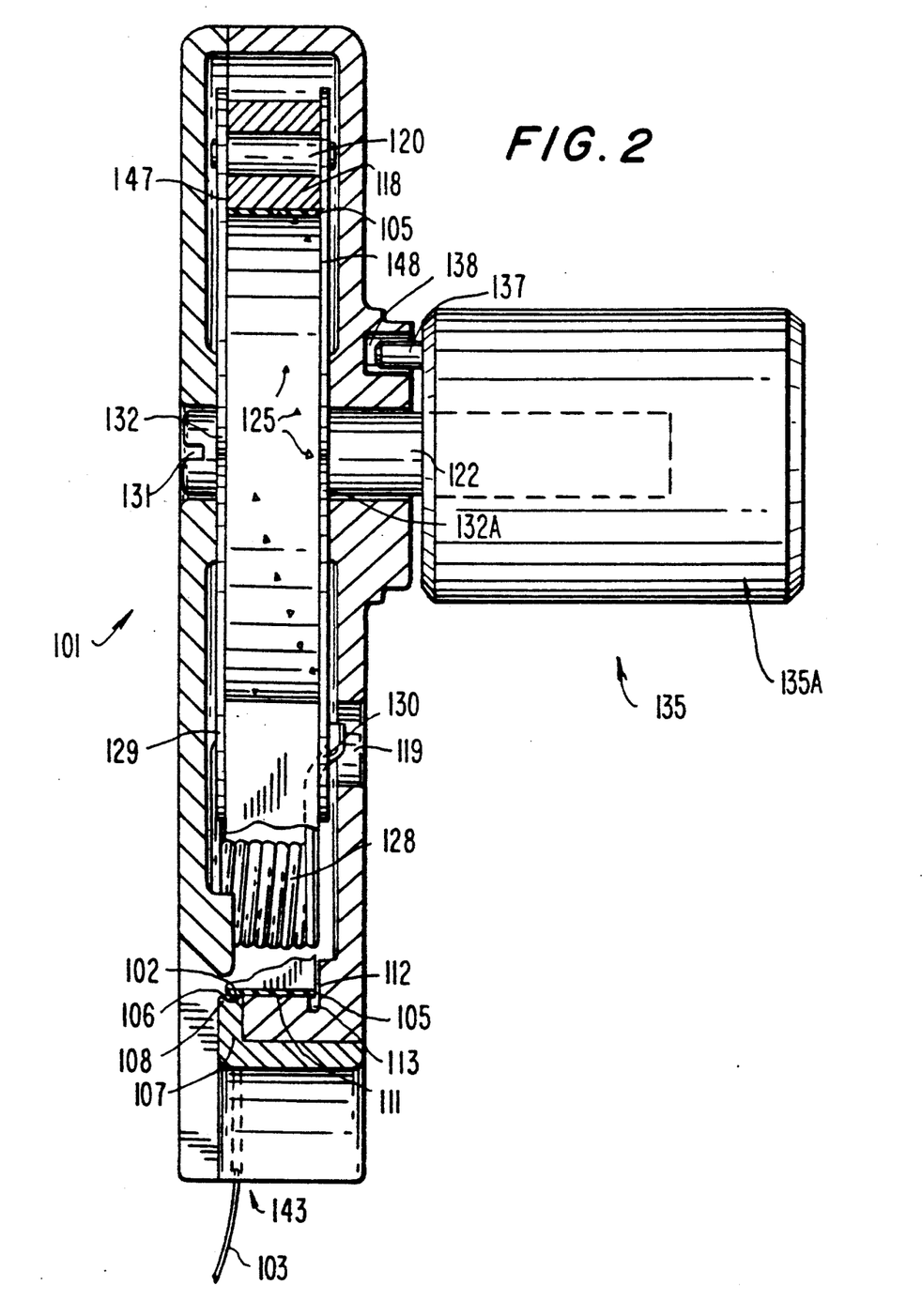
FIG. 2 is a partial cross-sectional view of the cassette and the driving mechanism knob taken along line 2—2 of FIG. 1.

Referring to FIGS. 1 and 2, suturing cassette device 100 comprises two general components: cassette 101 and driving mechanism 135. The cassette provides a housing which contains a mechanism for guiding and driving an arcuate suturing needle through a 360° suturing rotation. The driving mechanism may comprise a variety of different mechanisms for providing rotational driving power to the cassette.

Figures 8, 8A:
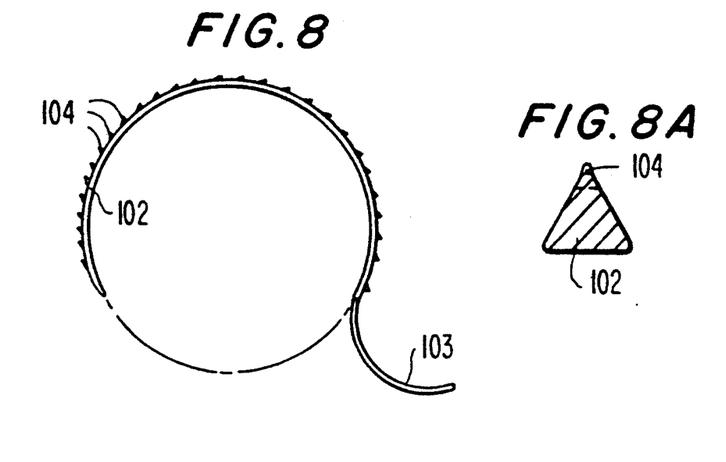
FIG. 8 is a side view of the barbed arcuate suturing needle according to the present invention.
FIG. 8A is a cross-sectional view of the barbed arcuate suturing needle shown in FIG. 8.

Barbed arcuate suturing needle 102 is shown in detail in FIGS. 8 and 8A. The needle is mounted in cassette 101 on saddle 107 for 360° rotation. Preferably, needle 102 has a three-edge cutting point, although alternative needle shapes are possible. Needle 102 also has a series of radially outward projecting barbs 104. Barbs 104 are angled, preferably acutely, to the rear of needle 102 and formed either completely around the outer perimeter of needle 102 or partially in zones to engage drive belt 105 as explained in greater detail below. The arrangement of barbs 104 on needle 102 is such that at least two barbs engage belt 105 at all times during rotation of the needle. The angle of barbs 104 facilitates said engagement and allows the barbs to pass freely through any biological tissue to be sutured.

Figure 7:
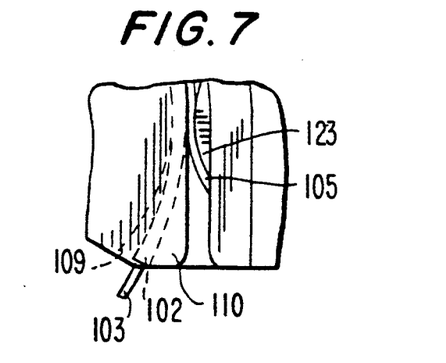
FIG. 7 is a partial front view illustrating the needle entrance area of the cassette shown in FIG. 1.

As indicated above, needle 102 rotates around and is supported on semi-circular saddle 107 (see FIG. 1). The length of needle 102 and geometry of saddle 107 are such that needle 102 is always in sliding contact with the saddle as it rotates therearound. That is, saddle 107 extends around an arc of slightly more than about 180° so needle 102, which also extends around an arc of more than about 180°, is always in sliding contact with the saddle. Formed in saddle 107, along its circumference, is needle guide groove 106 which ensures that needle 102 is retained within saddle 107 as it travels through its arcuate path (see FIGS. 2 and 3). Preferably, groove 106 has the same cross-sectional shape as the inside circumference of needle 102 allowing the needle to fit snugly in the groove. Also formed on saddle 107, along the outer edge of its circumference, is flange 108 which keeps needle 102 within saddle 107. As needle 102 rotates, it passes through open throat area 114 which accommodates biological tissue to be sutured. After passing through open throat area 114, needle 102 is funneled back into saddle 107 by ramps 109 and 110, formed at the entrance of the saddle (see FIG. 7).

Figure 3:
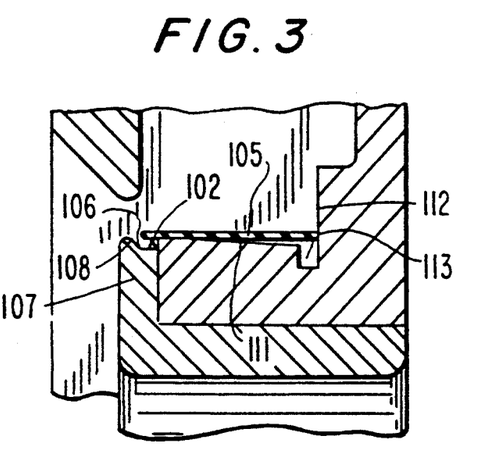
FIG. 3 is a cross-sectional view of the lower portion of the cassette shown in FIG. 1.

Referring to FIGS. 1, 2 and 3, a continuous-loop, needle drive belt 105, which passes over the needle at the bottom of cassette 101, drives needle 102 through its suturing rotation. Preferably, needle drive belt 105 is flat and made of a composite of materials. By constructing belt 105 of a strong inner core and a relatively pliable outer covering the belt is prevented from stretching and/or deforming while in storage or in use while also allowing needle barbs 104 to penetrate the surface of the belt for positive engagement therebetween. Alternative belt materials and manufacturing designs are possible, such as, sprocketed holes or recesses in the belt which are engaged by protrusions formed on the outer perimeter of needle 102.

Movement of belt 105 through cassette 101 is directed by a yoke assembly, a series of pulleys and rollers, and a number of other cooperating elements. The yoke assembly includes a pair of rollers 118 and 119 and drive drum 117 mounted on axles 120 and 121 and shaft 122, respectively. Rollers 118 and 119 are rotatably mounted on front and back plates 147 and 148 which together form a pivoted mounting bracket. The rollers press belt 105 onto drive drum 117. Drum 117 has raised protrusions or barbs 125 on its surface and is fixed to shaft 122 at its center of rotation. Projecting barbs 125 engage belt 105 as it passes around drum 117 to ensure positive engagement of the belt with the drive drum. Means 135 for rotating the drum are explained in detail below.

Figure 5:
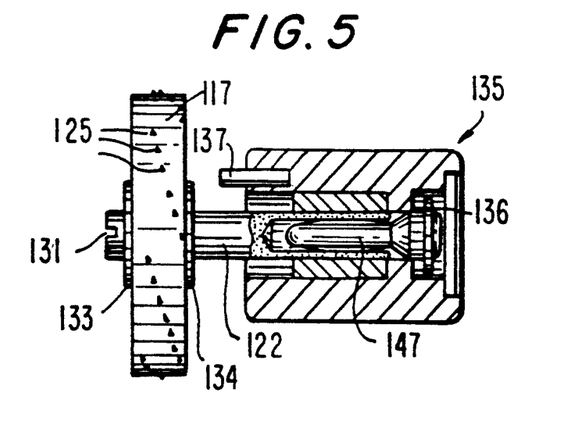
FIG. 5 is a partial cross-sectional side view of the barbed-drive drum attached to the driving mechanism taken along line 5—5 of FIG. 4.
Figure 6:
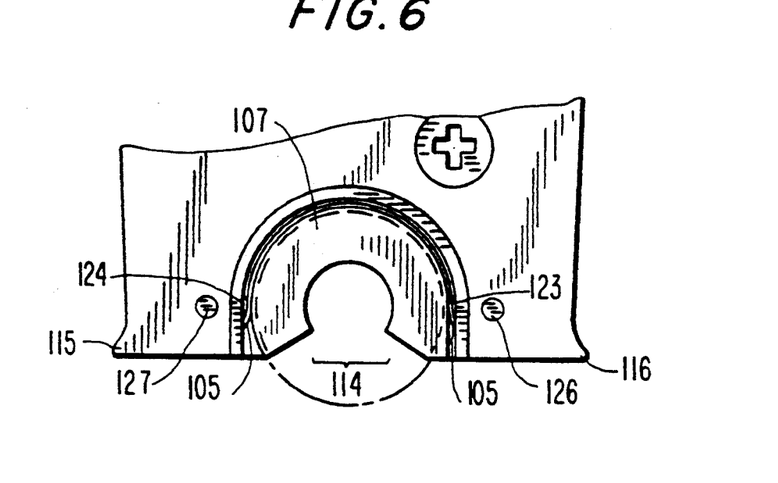
FIG. 6 is a partial front view illustrating the foot area of the cassette shown in FIG. 1.

To ensure the proper position of drum 117 along the length of shaft 122, there are two shoulder pieces or washers 133 and 134 which secure the position of drum 117 on the shaft (see FIG. 5). Washers 133 and 134 on shaft 122 are set into yoke positioning bearing holes 132 and 132A in front and back plates 147 and 148 respectively (see FIG. 2). Holes 132 and 132A are slightly elongated to allow the yoke assembly to seek its own center.

Working in conjunction with the yoke assembly are two rollers 123 and 124, which are rotatably mounted on fixed axles 126 and 127, respectively. Rollers 123 and 124 redirect belt 105 over needle 102 and maintain belt pressure thereagainst such that needle barbs 104 engage belt 105. Referring to FIG. 3, as belt 105 passes over needle 102, a belt guide 111 and belt edge guide 112 support and direct the belt through the lower portion of cassette 101 between rollers 123 and 124. Belt guide 111 is slightly sloped towards belt edge guide 112. This causes drive belt 105 to ride against belt edge guide 112 and stay properly positioned in the lower portion of cassette 101 rather than creep off belt guide 111 and interfere with the rotation of needle 102 and/or thread 103. At the point where belt guide 111 and belt edge guide 112 meet there is also a debris trough 113 which accommodates debris (e.g., tissue) picked up by belt 105 during operation of the device.

Also cooperating with the yoke assembly is spring 128 mounted between a cassette spring mounting hole 129 and yoke spring mounting hole 130 located in back plate 148. Spring 128 biases the yoke assembly thereby controlling the pressure belt 105 exerts on barbed drive drum 117 and needle 102 (as well as the needle on saddle 107). This also removes any slack from belt 105 so the belt can pass through cassette 101 without hinderance.

Figure 4:
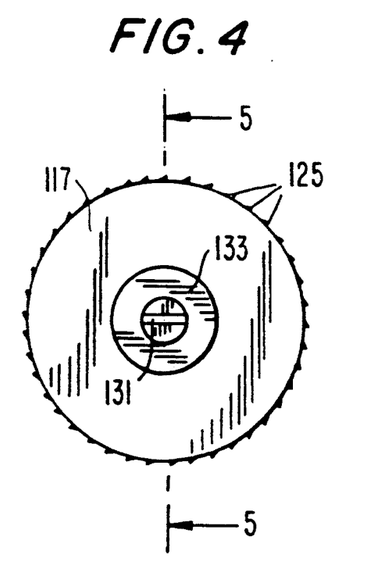
FIG. 4 is a front view of the barbed drive drum contained within the cassette shown in FIG. 1.

Preferably, drum 117 is made of a solid material. Alternatively, drum 117 can be hollowed out with a rim of suitable hard material that would support projecting barbs 125, or be made of a composite material with a hardened outer rim on which the barbs are formed. In a further alternative, drum 117 can also resemble a gear having tooth-like protrusions on its surface capable of engaging sprocket holes formed in the surface of belt 105.

Although barbs 125 on the surface of drum 117 are shown spaced apart for purposes of spreading out the damage caused by the barbs to the surface of belt 105, other patterns and densities of barbs or protrusions can be used to avoid off center pull of belt 105, to reduce belt wear, or to accommodate a particular sized needle 102 or cassette 101. It should also be noted that barbs 125 on drum 117 engage the opposite side of belt 105 that needle barbs 104 engage. This prevents accelerated deterioration of the needle side of belt 105 which could lead to misregistration between needle 102 and the belt.

Shaft 122 is provided with a screwdriver slot 131 on one end and a bored out hole or other feature on its drive end for mounting a driving mechanism to cassette 101. Although cassette 101 is designed to drive belt 105 and needle 102 in only one direction—i.e. in the direction of the needle's leading point—screwdriver slot 131 allows a user of the device to circumvent the one-way drive feature and reverse or otherwise reposition needle 102 when cassette 101 is clear of a patient.

If the device jams during the suturing process, a user can easily and quickly disassemble cassette 101 from needle 102 with minimal trauma to a patient, after which the user can finish suturing by hand. As such, cassette 101 is meant to be disposable, which is helpful in preventing the spread of infection, and/or capable of being factory rebuilt after use.

Referring in particular to FIGS. 2 and 5, cassette 101 is designed to attach to various driving mechanisms or power heads which are either manually or power driven. One of the simplest drive attachments is a knob such as knob 135 which has a knurled gripping surface 135A as shown in FIG. 2. Knob 135 allows a user to manually rotate needle 102 once the device is set for suturing. Knob 135 has means 147 for mounting shaft 122 to the knob, for example, a spring loaded pin which is frictionally received in a bored-out hole of the shaft. Preferably, knob 135 is fitted with a one-way roller clutch 136 to ensure rotation of needle 102 in only one direction, although a spring clutch can also be utilized. Once a suture is completed, clutch 136 permits a user to rotate knob 135 back to its original starting position without the needle moving.

Alternatively, a foot operated bladder pump, or an electronically or mechanically powered pump which forces a medically safe hydraulic fluid through a length of commercially available hose, can be used to provide a pressure force to drive needle 102.

Knob 135 is fitted with a pin 137 which engages slot 138 located on the backside of cassette 101. Slot 138 defines an arc of slightly less than about 180° and therefore restricts rotation of knob 135 to just less than one-half of a revolution. Drum 117 is designed approximately twice as large as the circumference of needle 102. Therefore, by rotating knob 135 just less than a half revolution, needle 102 almost completes a full revolution. By restricting needle 102 from making a complete revolution, needle 102 is safely prevented from reentering the patient a second time. The point of needle 102 is also safely protected in cassette 101 avoiding injury or the spread of infection to a user of the device. This becomes particularly important for the user who must preset suture thread 103 about foot area 143 of the cassette after each completed suture. It is contemplated that the same objective can be achieved by making slot 138 and drum 117 a variety of different sizes—e.g., make slot 138 a full 180° and the circumference of drum 117 slightly less than twice that of needle 102.

Figure 9:
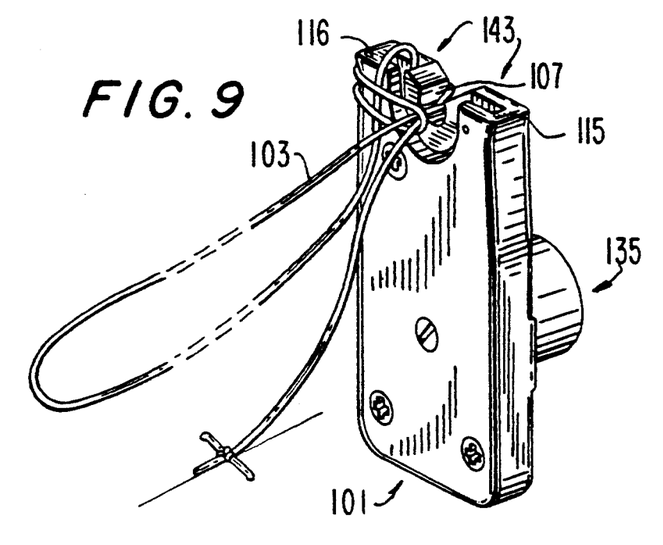
FIG. 9 is a perspective view of the present invention illustrating the presetting of the suture thread on the foot area of the cassette.
Figure 10:
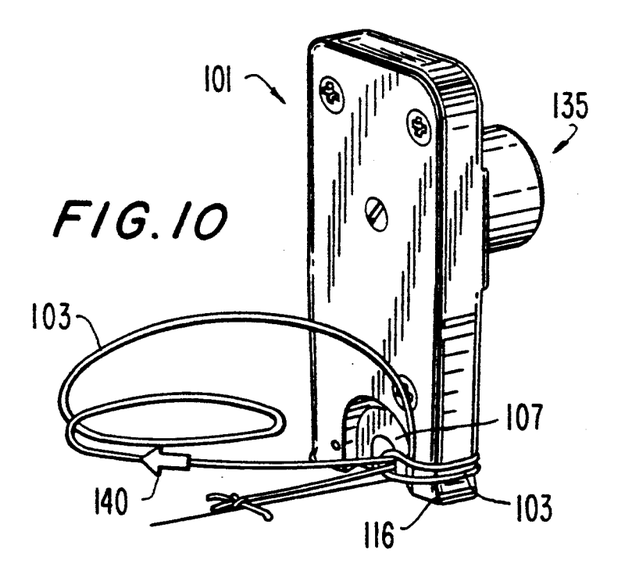
FIG. 10 is a perspective view of the present invention illustrating the method for removing slack from the preset suture thread shown in FIG. 9.

Referring to FIGS. 9 and 10, extending outwardly from foot area 143 of cassette 101, on either side of open throat area 114, are two sloped extensions 115 and 116. As shown in FIG. 9, prior to suturing, suture thread 103 is preset to form a knot by looping the thread around sloped extension 116 and through open throat area 114. As shown in FIG. 10, once thread 103 is preset, a user must place foot area 143 of cassette 101 over a target area and optionally remove any slack in the thread by pulling on the thread as shown by arrow 140. This reduces the tendency of thread 103 to tangle and reduces the amount manipulation required of the thread after needle 102 has completed its cycle. Any thread slack extending from the rear of needle 102 is dressed to the outside of cassette 101 to prevent thread 103 from getting caught up in needle guide 106 and jamming the movement of needle 102.

Figure 11:
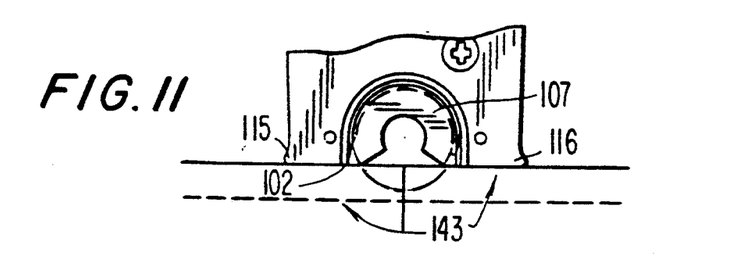
FIG. 11 is a front view of the present invention illustrating the path of the suturing needle through biological tissue.
Figure 12:
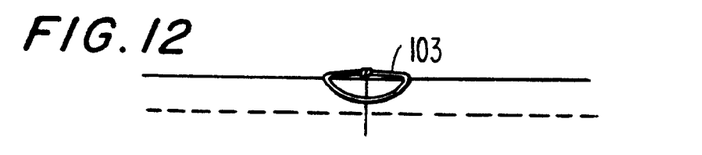
FIG. 12 is a sectional view of a suture formed in tissue by the present invention as shown in FIG. 11.
Figure 13:
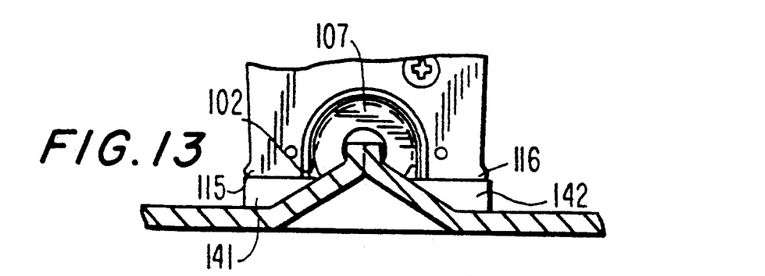
FIG. 13 is a front view of the present invention utilizing a mechanism for pinching together two sides of biological tissue.
Figure 14:
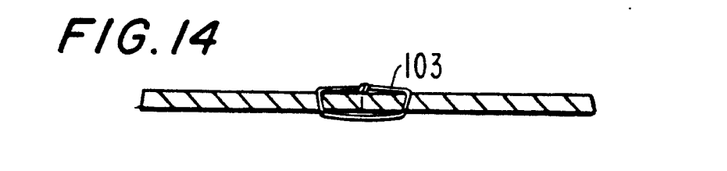
FIG. 14 is a sectional view of a suture formed in tissue by the present invention as shown in FIG. 13.
Figure 15:
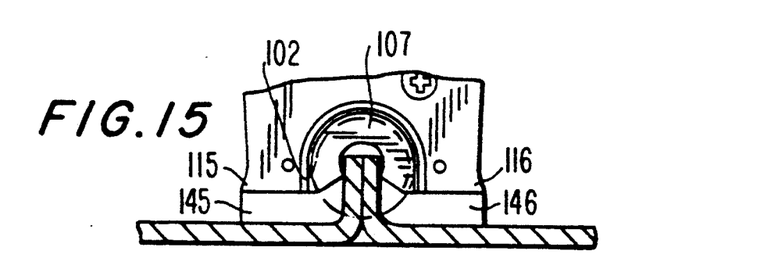
FIG. 15 is a front view of the present invention utilizing another mechanism for pinching together two sides of biological tissue.
Figure 16:
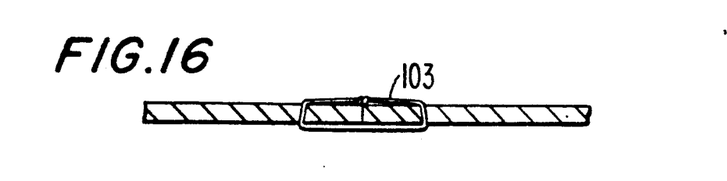
FIG. 16 is a sectional view of a suture formed in tissue by the present invention as shown in FIG. 15.

Referring to FIGS. 11 and 12, cassette suturing apparatus 100 is capable of suturing an incision or tear without having to pinch together opposite sides of the tissue to be sutured. However, there are circumstances which may require tissue to be drawn up into open throat area 114 such that needle 102 can pass freely through the tissue; e.g., to avoid suturing the tissue to any underlying organ. Referring to FIG. 13, there can be incorporated into foot area 143 two wedged shaped holding members 141 and 142, each having a slightly elongated base, which permit a user to hold tissue (which has been pinched together prior to suturing) in open throat area 114. FIG. 14 shows the completed suture formed by this method. Similar to holding members 141 and 142, FIG. 15 shows two alternatively shaped holding members 144 and 145 which are likewise capable of holding tissue to be sutured securely in open throat area 114 during a suturing procedure. Holding members 144 and 145 are rectangular in shape having an upward turned lip on their top surface closest to open throat area 114. FIG. 16 depicts the completed suture formed with holding members 145 and 146. Vacuum grippers can also be incorporated into foot area 143 of cassette 101 to hold tissue securely in place during suturing procedures. Alternatively, members 141 and 142, or members 145 and 146, can be slidably mounted to the foot area 143 of cassette 101 for pinching together opposite sides of an incision or tear. Each pair of cooperating members are able to converge on the area of tissue to be sutured and thereby draw the tissue up into the open throat area 114 of the cassette. Needle 102 can then pass through the tissue without suturing it to any underlying organ.

I claim:

1. An apparatus for suturing, comprising:
   a housing;
   a flexible, continuous loop drive element mounted within the housing for circulation therein;
   means for circulating the continuous loop drive element, including a rotating drive member mounted in the housing having a plurality of first spaced projecting means for engaging the continuous loop drive element, wherein said loop element passes around said drive member and is circulated through said housing by rotation of said member;

means detachable from said housing and rotating drive member for driving said rotating drive member; and an arcuate suturing needle mounted at an end of the housing for 360° rotation through a closed path, said needle having a leading point and a plurality of second spaced projecting means for engaging the continuous loop drive element.

2. The apparatus of claim 1, wherein said circulating means comprises:

a shaft having first and second ends rotatably mounted to the housing for rotation around a transverse axis of the housing, wherein said rotating drive member comprises a circular drum mounted on the shaft between said first and second ends for rotation within the housing and around the transverse axis, said plurality of first spaced projecting means for engaging the continuous loop element being disposed on the drum; and means for engaging the first end of the shaft from outside the housing with said detachable driving means to rotate and drive the circular drum.

3. The apparatus of claim 2, wherein said shaft further comprises a slot at its second end, said slot being accessible to a user from outside the housing and capable of receiving an element for rotating said shaft in either rotational direction around the transverse axis.

4. The apparatus of claim 1 wherein said means for driving the rotating drive member includes a pin, mounted for rotation with the driving means, extending in the direction of the housing, wherein said housing defines a slot having an included angle of slightly less than about 180° for receiving the pin in the extended position to limit rotation of the driving means to slightly less than one-half of a revolution, and said circular drum has a circumference about twice as large as the circumference of the arcuate needle.

5. The apparatus of claim 1, wherein the housing defines an open throat area at the end through which the needle passes in said closed path; and said apparatus further comprises means adjacent to the throat area for pinching together material to be sutured.

6. An apparatus for suturing, comprising:
a housing;
a continuous loop drive element mounted within the housing for circulation therein;
means for circulating the continuous loop drive element, including a rotating member having a plurality of spaced projecting means for engaging the continuous loop drive element;
an arcuate suturing needle mounted at an end of the housing for 360° rotation through a closed path, said needle having a leading point and a plurality of spaced projecting means for engaging the continuous loop drive element, said projecting means being arranged on the needle such that at least two of said projecting means engage the continuous loop element at all times during rotation of the needle;
means for circulating the continuous loop drive element, said means comprising a shaft having first and second ends rotatably mounted to the housing for rotation around a transverse axis of the housing, a circular drum mounted on the shaft between said first and second ends for rotation within the housing and around the transverse axis, said drum having a plurality of spaced projecting means for engaging the continuous loop drive element;
drive means for rotating the shaft including clutch means for limiting said rotation of the shaft to a single direction which causes the arcuate needle to rotate in the direction of its leading point; and
quick disconnect means for connecting and disconnecting said drive means to the shaft.

7. The apparatus of claim 6, wherein the driven rotating member is carried on a bracket member having a first end pivotally mounted to the housing, and said tensioning means comprises a spring cooperating with the bracket member to bias the rotating member against said continuous loop drive element.

8. The apparatus of claim 6, wherein the arcuate needle defines an arc having an included angle greater than about 180°, and wherein said apparatus further comprises:

a saddle member mounted in the housing having an arcuate outer surface slideably mating with and received inside the arc of the arcuate needle, said outer surface defining an arc also having an included angle greater than about 180°, said saddle member further defining an open throat area opposite said outer surface in which material to be sutured is received; and means for tensioning said continuous loop drive element around the arcuate outer surface with the needle received therebetween such that the needle projecting means are maintained in engagement with the continuous loop drive element.

9. The apparatus of claim 6, wherein the drive means for rotating the shaft further comprises a pin mounted for rotation with the drive means extending in the direction of the housing, wherein said housing defines a slot having an included angle of slightly less than about 180° for receiving the pin in the extended position to limit rotation of the drive means to slightly less than one-half of a revolution, and said circular drum has a circumference about twice as large as the circumference of the arcuate needle.

10. An apparatus for suturing, comprising:
a housing;
a continuous loop drive element mounted within the housing for circulation therein;
means for circulating the continuous loop drive element, including a rotating member having a first plurality of spaced projecting means for engaging the continuous loop drive element;
an arcuate suturing needle mounted for rotation having a second plurality of spaced projecting means for engaging the continuous loop drive element and defining an arc having an included angle greater than about 180°;
a saddle member mounted in the housing having an arcuate outer surface slideably mating with and received inside the arc of the arcuate needle, said outer surface defining an arc also having an included angle greater than about 180°, said saddle member further defining an open throat area opposite said outer surface in which material to be sutured is received; and means for tensioning said continuous loop drive element around the arcuate outer surface with the needle received therebetween such that the needle projecting means are maintained in engagement with the continuous loop drive element.

11. The apparatus of claim 10, wherein the rotating member is carried on a bracket member having a first end pivotally mounted to the housing, and said tensioning means comprises a spring cooperating with the bracket member to bias the rotating member against said continuous loop drive element.

12. An apparatus for suturing, comprising:
a housing;
a continuous loop drive element mounted within the housing for circulating therein;
a shaft having first and second ends rotatably mounted to the housing for rotation;
a circular drum mounted on the shaft between said first and second ends for rotation within the housing, said drum having a first plurality of spaced projecting means for engaging the continuous loop element;
an arcuate suturing needle mounted for rotation having a leading point and second plurality of spaced projecting means for engaging the continuous loop drive element; and
a knob assembly engaging the first end of the shaft, said knob assembly including clutch means for limiting rotation of the shaft to a single direction which causes the arcuate needle to rotate in the direction of its leading point.

13. The apparatus of claim 12, wherein the knob assembly includes a pin mounted for rotation with said assembly, said pin biased outward to an extended position in the direction of the housing, wherein the housing defines a slot at a predetermined location for receiving the pin in the extended position to stop rotation of the knob at said predetermined location after a 360° rotation.

14. An apparatus for suturing, comprising:
a housing;
a continuous loop drive element mounted within the housing for circulation therein;
means for circulating the continuous loop drive element, including a rotating member mounted in the housing having a plurality of first spaced projecting means for engaging the continuous loop drive element; and
an arcuate suturing needle mounted at an end of the housing for 360° rotation through a closed path, said needle having a leading point and a plurality of second spaced projecting means for engaging the continuous loop drive element, wherein said second spaced projecting means are arranged on the needle such that at least two of said projecting means engage the continuous loop element at all times during rotation of the needle.

* * * * *